(12) United States Patent
Hiemstra et al.

(10) Patent No.: US 11,556,095 B2
(45) Date of Patent: Jan. 17, 2023

(54) MODULAR SENSING ASSEMBLY FOR AN ELECTRONIC DEVICE

(71) Applicant: Apple Inc., Cupertino, CA (US)

(72) Inventors: Daniel J. Hiemstra, San Jose, CA (US); Erik G. de Jong, San Francisco, CA (US); Kevin F. Holz, Santa Cruz, CA (US); Michael B. Wittenberg, Sunnyvale, CA (US); Timothy D. Koch, Santa Cruz, CA (US)

(73) Assignee: Apple Inc., Cupertino, CA (US)

( * ) Notice: Subject to any disclaimer, the term of this patent is extended or adjusted under 35 U.S.C. 154(b) by 406 days.

(21) Appl. No.: 16/849,548

(22) Filed: Apr. 15, 2020

(65) Prior Publication Data

US 2021/0325834 A1    Oct. 21, 2021

(51) Int. Cl.
| | |
|---|---|
| *A61B 5/021* | (2006.01) |
| *G04G 21/02* | (2010.01) |
| *G04G 17/08* | (2006.01) |
| *A61B 5/024* | (2006.01) |
| *A61B 5/00* | (2006.01) |

(52) U.S. Cl.
CPC ....... *G04G 21/025* (2013.01); *A61B 5/02438* (2013.01); *A61B 5/681* (2013.01); *G04G 17/08* (2013.01)

(58) Field of Classification Search
CPC .............. A61B 5/0006; A61B 5/02427; A61B 5/02438; A61B 5/0245; A61B 5/681; A61B 5/6898; A61B 5/7405; A61B 2090/065; A61B 2562/0219; G06F 1/163; G06F 1/3231; G06F 21/32; G04G 21/00; G04G 21/02; G04G 21/08; G04G 17/08; G06Q 20/321; H04R 2499/11
See application file for complete search history.

(56) References Cited

U.S. PATENT DOCUMENTS

| | | |
|---|---|---|
| 9,442,525 B2 | 9/2016 | Choi et al. |
| 9,558,336 B2 | 1/2017 | Lee |
| 9,861,286 B1 | 1/2018 | Islam |
| 10,181,021 B2 | 1/2019 | Venkatraman et al. |
| 10,278,591 B2 | 5/2019 | Gil |
| 10,376,164 B2 | 8/2019 | Presura et al. |

(Continued)

FOREIGN PATENT DOCUMENTS

| | | |
|---|---|---|
| EP | 3451117 | 3/2019 |
| WO | WO 13/173838 | 11/2013 |

OTHER PUBLICATIONS

International Search Report and Written Opinion dated Jul. 8, 2021, PCT/US2021/026982, 11 pages.
U.S. Appl. No. 17/013,295, filed Sep. 4, 2020, Allec et al.

*Primary Examiner* — Lawrence S Galka
(74) *Attorney, Agent, or Firm* — Brownstein Hyatt Farber Schreck, LLP

(57) ABSTRACT

A modular sensing assembly may be used to detect user inputs at an electronic device. Example user inputs include touch inputs, fingerprint inputs, translational inputs, audio inputs, biometric inputs, and the like. Inputs received using the modular sensing assembly may be used to control a graphical output of a display of the electronic device. A modular sensing assembly may be configured, for example, as a power button, a key of a keyboard, a control button (e.g., volume control), a home button, a watch crown, and so on.

20 Claims, 9 Drawing Sheets

(56) References Cited

U.S. PATENT DOCUMENTS

| | | |
|---|---|---|
| 10,599,192 B2 | 3/2020 | Younes et al. |
| 2008/0049980 A1 | 2/2008 | Castaneda et al. |
| 2016/0129279 A1 | 5/2016 | Ferolito |
| 2017/0119262 A1* | 5/2017 | Shim ........................ H04W 4/70 |
| 2018/0235483 A1* | 8/2018 | Mouradian ............. G06F 1/163 |
| 2019/0072912 A1* | 3/2019 | Pandya .................. G04G 21/08 |
| 2019/0083034 A1* | 3/2019 | Shim .................. A61B 5/14551 |
| 2020/0041962 A1 | 2/2020 | Beyhs |

* cited by examiner

MODULAR SENSING ASSEMBLY FOR AN ELECTRONIC DEVICE

FIELD

Embodiments relate generally to an electronic watch or other electronic device. More particularly, the described embodiments relate a modular sensing assembly for receiving multiple types of inputs at an electronic watch or other electronic device.

BACKGROUND

Many traditional electronic devices include buttons, keys, or other similar input mechanisms. Many traditional input mechanisms are difficult to seal and may introduce one or more paths through which contaminants may enter the device. Furthermore, many traditional mechanisms are structurally integrated in a way that does not facilitate component-level testing or easy repair. The embodiments described herein are directed to electronic devices having a modular sensing assembly that may address these and other issues that are associated with some traditional input mechanisms.

SUMMARY

Embodiments of the systems, devices, methods, and apparatuses described in the present disclosure are directed to a modular sensing assembly for receiving multiple types of inputs at an electronic device.

One embodiment may take the form of an electronic watch that includes a housing defining an interior volume and having a sidewall and a recess formed in the sidewall, a processing unit positioned within the interior volume, a display, and a modular sensing assembly disposed in the recess and operably coupled to the processing unit. The modular sensing assembly may include an assembly enclosure that includes a cover defining a portion of an exterior surface of the electronic watch and a trim member extending around a perimeter of the cover. The modular sensing assembly may further include an electrocardiograph electrode disposed on the cover and configured to detect an electrocardiograph signal. The modular sensing assembly may further include a sensing sub-assembly positioned between the cover and the sidewall and at least partially surrounded by the trim member. The sensing assembly may include a touch sensor configured to detect a touch input on the cover and an audio sensor configured to detect an audio input. The modular sensing assembly may further include a translation sensor positioned beneath the cover and configured to detect a translational input to the cover and a sealing member positioned between the trim member and the housing and configured to exclude contaminants from the interior volume. The display may be configured to provide a graphical output that is responsive to the electrocardiograph signal, the touch input, the audio input, and the translational input.

Another embodiment may take the form of an electronic watch that includes a display, a processing unit operably coupled to the display, a housing at least partially surrounding the display and having a sidewall and defining a recess formed in the sidewall. The electronic watch may further include a modular sensing assembly disposed in the recess. The modular sensing assembly may include a cover defining an input surface, a capacitive sensor positioned beneath the input surface and configured to detect a touch input on the input surface and detect a fingerprint input on the input surface. The modular sensing assembly may further include an audio sensor positioned beneath the cover and configured to detect an audio input through an opening in the cover. The modular sensing assembly may further include a translation sensor positioned beneath the cover and configured to detect a translational input at the input surface. The modular sensing assembly may further include a trim member at least partially surrounding the cover, the capacitive sensor, and the audio sensor. The display may be configured to provide a graphical output that is responsive to the touch input, the fingerprint input, the audio input, and the translational input.

Another embodiment may take the form of an electronic device that include a housing defining a recess and a modular sensing assembly disposed in the recess. The modular sensing assembly may include an assembly enclosure that includes a cover defining an input surface and configured to translate in response to a translational input and a trim member extending around a perimeter of the cover. The modular sensing assembly may further include a touch sensor positioned at least partially within the assembly enclosure and configured to detect a touch input on the input surface and detect a fingerprint input on the input surface. The modular sensing assembly may further include an audio sensor positioned at least partially within the assembly enclosure and configured to detect an audio input through an opening in the cover. The modular sensing assembly may further include an electrocardiograph electrode disposed on an exterior surface of the cover and configured to detect an electrocardiograph signal. The modular sensing assembly may further include a dome switch positioned beneath the cover and configured to detect the translational input by actuating in response to the cover translating. The modular sensing assembly may further include a sealing member positioned between the trim member and an inside surface of the recess, the sealing member configured to deform in response to the translational input.

In addition to the example aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1A:
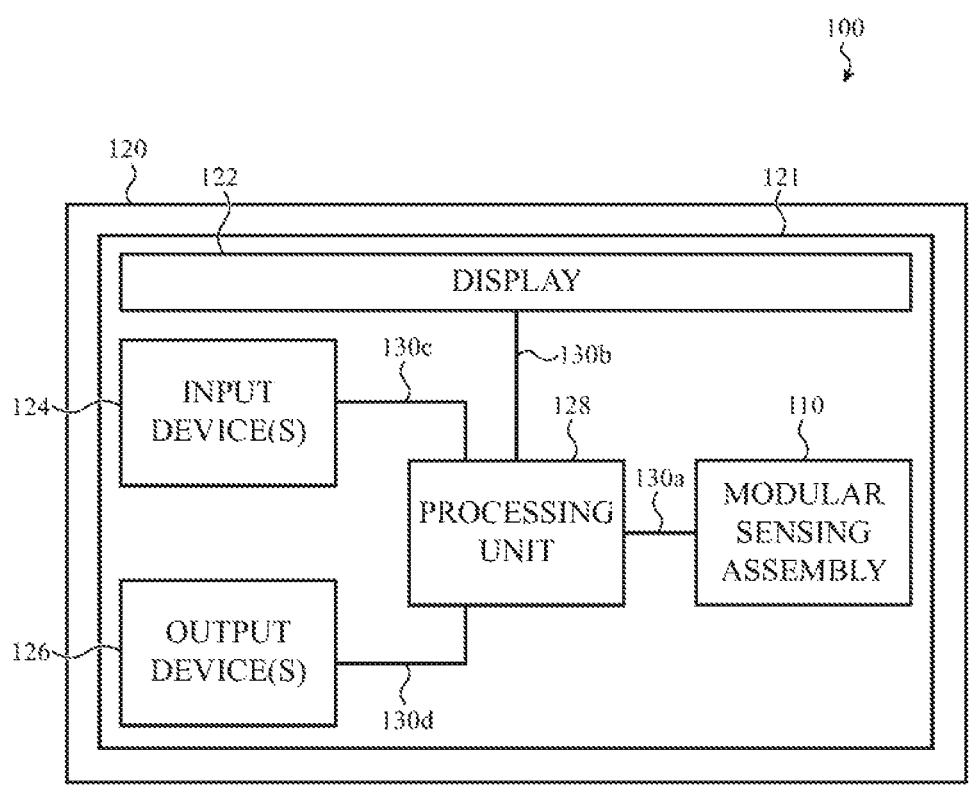
FIG. 1A illustrates a block diagram of an example electronic device that may incorporate a modular sensing assembly.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The following disclosure relates to a modular sensing assembly for use as part of an electronic device. The modular sensing assembly may receive multiple different types of user inputs. Example user inputs include touch inputs, fingerprint inputs, translational inputs, audio inputs, biometric inputs, and the like. Inputs received using the modular sensing assembly may be used to control a graphical output of a display of the electronic device. A modular sensing assembly may be configured, for example, as a power button, a key of a keyboard, a control button (e.g., volume control), a home button, a watch crown, and so on.

Combining multiple components in a modular sensing assembly provides advantages over traditional input mechanisms. Advantages include reducing device component redundancy and manufacturing complexity. For example, a modular sensing assembly may include a single sealing member that provides a seal around all of the components of the modular sensing assembly and/or between the modular sensing assembly and a device housing. This may reduce the overall number of parts required to assemble the electronic device, which may reduce manufacturing complexity and cost as well as minimize a size of the device. As another example, multiple components of the modular sensing assembly may be operably coupled to a processing unit using one or more common connectors and/or common passages into an interior volume of the device.

The modular sensing assembly may be positioned at least partially within a housing of an electronic device. Example inputs received by the modular sensing assembly may include touch inputs, translational inputs, fingerprint inputs, audio inputs, electrocardiograph signals, and the like. The modular sensing assembly may provide one or more outputs. Example outputs provided by the modular sensing assembly include audio outputs, haptic outputs, visual outputs, and the like.

As discussed in more detail below, the modular sensing assembly may include multiple sensors, sub-assemblies, and/or other components positioned within an assembly enclosure. Combining multiple components in a modular sensing assembly provides advantages over traditional input mechanisms. Advantages include reducing device component redundancy and manufacturing complexity. For example, a modular sensing assembly may include a single sealing member that provides a seal around all of the components of the modular sensing assembly and/or between the modular sensing assembly and a device housing. As another example, multiple components of the modular sensing assembly may be operably coupled to a processing unit using one or more common connectors and/or common passages into the interior volume of the electronic device.

The modular sensing assemblies described herein may include a sealing member that inhibits contaminants from entering the interior volume and/or a housing of the electronic device. "Contaminants," as used herein, may be used to refer to foreign matter that is not intended to be present in the interior volume or the electronic device. Example contaminants include liquids, such as water, and solid matter such as lint, dust, and food particles. In one embodiment, a sealing member is positioned between one or more components of a modular sensing assembly and one or more surfaces of the housing of the electronic device.

The term "attached," as used herein, may be used to refer to two or more elements, structures, objects, components, parts or the like that are physically affixed, fastened, and/or retained to one another. The term "coupled," as used herein, may be used to refer to two or more elements, structures, objects, components, parts or the like that are physically attached to one another, operate with one another, communicate with one another, are in electrical connection with one another, and/or otherwise interact with one another. Accordingly, while elements attached to one another are coupled to one another, the reverse is not required. As used herein, "operably coupled" or "electrically coupled" may be used to refer to two or more devices that are coupled in any suitable manner for operation and/or communication, including wiredly, wirelessly, or some combination thereof.

These and other embodiments are discussed with reference to FIGS. 1A-4. However, those skilled in the art will readily appreciate that the detailed description given herein with respect to these figures is for explanatory purposes only and should not be construed as limiting.

FIG. 1A illustrates a block diagram of an example electronic device 100 that may incorporate a modular sensing assembly 110. The electronic device 100 may include a display 122, one or more input devices 124, one or more output devices 126, and the modular sensing assembly 110. Each of the components of the electronic device 100 may be operably coupled to a processing unit 128. The electronic device 100 may include a housing 120. The components of the electronic device 100 may be positioned at least partially within an interior volume 121 of the housing 120.

The modular sensing assembly 110 may be positioned at least partially within the housing 120 of the electronic device 100, and may be configured to receive inputs and/or provide outputs. Example inputs received by the modular sensing assembly 110 may include touch inputs, translational inputs, fingerprint inputs, audio inputs, electrocardiograph signals, and the like. Example outputs provided by the modular sensing assembly 110 may include audio outputs, haptic outputs, visual outputs, and the like. The modular sensing assembly 110 may be operably coupled to the processing unit 128, for example by a connector 130a.

As discussed in more detail below, the modular sensing assembly 110 may include multiple sensors, sub-assemblies, and/or other components positioned within an assembly enclosure. Combining multiple components in a modular sensing assembly 110 provides advantages over traditional input mechanisms. Advantages include reducing device component redundancy and manufacturing complexity. For example, a modular sensing assembly 110 may include a single sealing member that provides a seal around all of the components of the modular sensing assembly 110 and/or between the modular sensing assembly 110 and the housing 120. As another example, multiple components of the modular sensing assembly 110 may be operably coupled to the processing unit using one or more common connectors and/or common passages into the interior volume 121.

In various embodiments, the display 122 may be positioned at least partially within the interior volume 121 of the housing 120. The display 122 provides a graphical output, for example associated with an operating system, user interface, and/or applications of the electronic device 100. In one embodiment, the display 122 includes one or more sensors and is configured as a touch-sensitive (e.g., single-touch, multi-touch) and/or force-sensitive display to receive inputs from a user. The display 122 is operably coupled to the processing unit 128 of the electronic device 100, for example by a connector 130b. In some cases, the graphical output of the display 122 is visible along at least a portion of an external surface of the electronic device 100.

In various embodiments, a graphical output of the display 122 is responsive to inputs provided at the display, one or more input devices 124, and/or one or more modular sensing assemblies 110. For example, the processing unit 128 may be configured to modify the graphical output of the display 122 in response to determining an electrocardiogram, receiving rotational inputs, receiving translational inputs, receiving touch inputs, receiving fingerprint inputs, receiving audio inputs, and the like. In some cases, a haptic output provided by the modular sensing assembly 110 corresponds to the graphical output of the display 122. In some cases, the modular sensing assembly 110 may produce a haptic output that is coordinated with a change in the graphical output of the display 122. For example, the haptic output may be produced at or near the same time as the change in the graphical output of the display 122. In some cases, a time that the haptic output is produced overlaps a time that the graphical output of the display 122 changes.

The display 122 can be implemented with any suitable technology, including, but not limited to liquid crystal display (LCD) technology, light emitting diode (LED) technology, organic light-emitting display (OLED) technology, organic electroluminescence (OEL) technology, or another type of display technology. In some cases, the display 122 is positioned beneath and viewable through the cover.

Broadly, the input devices 124 may detect various types of input, and the output devices 126 may provide various types of output. The modular sensing assembly 110 may be an example of an input device 124. Similarly, the modular sensing assembly 110 may be an example of an output device 126. The processing unit 128 may be operably coupled to the input devices 124 and the output devices 126, for example by connectors 130c and 130d, respectively. The processing unit 128 may receive input signals from the input devices 124, in response to inputs detected by the input devices. The processing unit 128 may interpret input signals received from one or more of the input devices 124 and transmit output signals to one or more of the output devices 126. The output signals may cause the output devices 126 to provide one or more outputs. Detected input at one or more of the input devices 124 may be used to control one or more functions of the electronic device 100.

In some cases, one or more of the output devices 126 may be configured to provide outputs that are dependent on, or manipulated in response to, the input detected by one or more of the input devices 124. The outputs provided by one or more of the output devices 126 may also be responsive to, or initiated by, a program or application executed by the processing unit 128 and/or an associated companion device. Examples of suitable processing units, input devices, output devices, and displays, are discussed in more detail below with respect to FIG. 4.

Figure 1B:
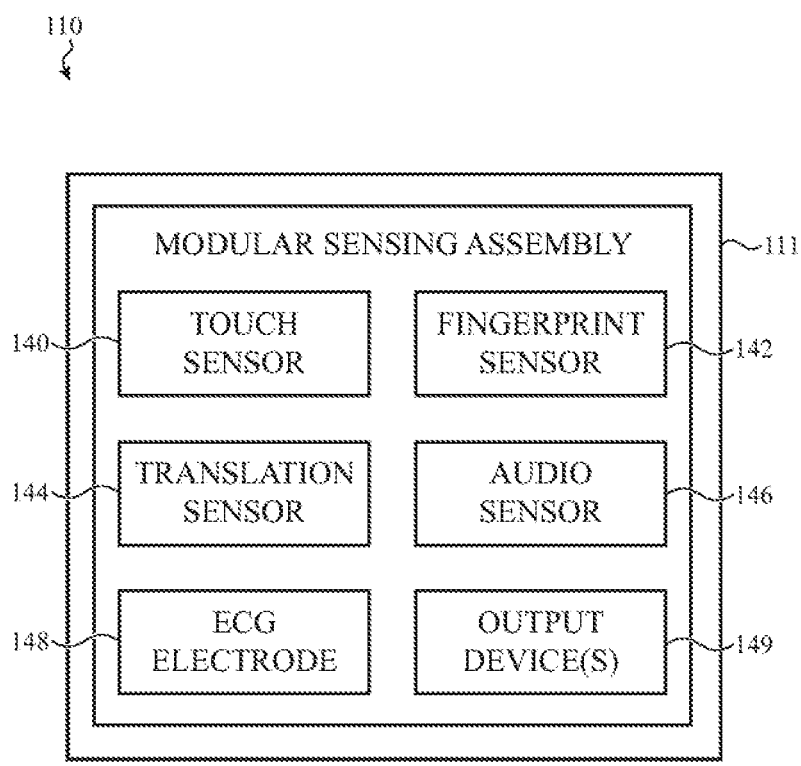
FIG. 1B illustrates a block diagram of the example modular sensing assembly of FIG. 1A.

FIG. 1B illustrates a block diagram of the example modular sensing assembly 110 of FIG. 1A. The modular sensing assembly 110 may include a touch sensor 140, a fingerprint sensor 142, a translation sensor 144, an audio sensor 146, an electrocardiograph (ECG) electrode 148, and one or more output devices 149. As noted above, the components of the modular sensing assembly 110 may be positioned at least partially within an assembly enclosure 111.

The touch sensor 140 can be any suitable device for detecting touch inputs the modular sensing assembly 110. As used herein, "touch inputs" may refer to any contact or near-contact with one or more input surfaces of the modular sensing assembly 110 by a user (e.g., a user's finger) or another object. Touch inputs may be taps, presses, gestures (e.g., swipes), and the like.

The touch sensor 140 may be implemented as a capacitive sensor, a resistive sensor, a contact sensor, a magnetic sensor, an optical sensor, an ultrasonic sensor, and so on. The touch sensor 140 may provide a signal in response to a touch input that may indicate that the touch input occurs, a type of input (e.g., tap, press, gesture, etc.), where an input occurs, and/or a measure of the input (e.g., a force measurement). In some cases, the modular sensing assembly 110 includes a cover that defines an input surface on an exterior surface of the modular sensing assembly, and the touch sensor 140 may be positioned beneath the cover of the modular sensing assembly 110 to detect touch inputs on or near the input surface.

Outputs provided by the electronic device 100 may be responsive to touch inputs detected using the touch sensor 140. For example, graphical outputs provided by the display 122 and/or audio outputs provided by an audio output device may be responsive to touch inputs detected using the touch sensor 140.

The fingerprint sensor 142 can be any suitable device for detecting fingerprint inputs at the modular sensing assembly 110. As used herein, "fingerprint inputs" may refer to any representation of a user's fingerprint, including a fingerprint image, a fingerprint map, and the like. Fingerprint inputs may be used by the processing unit 128 to perform authentication operations at the electronic device 100.

The fingerprint sensor 142 may be implemented as a capacitive sensor, a resistive sensor, a contact sensor, a magnetic sensor, an optical sensor, an ultrasonic sensor, a camera, and so on. The fingerprint sensor 142 may provide a signal in response to a fingerprint input that may contain information related to the fingerprint input. In some cases, the fingerprint sensor 142 may be positioned beneath the cover of the modular sensing assembly 110 to detect fingerprint inputs on or near the input surface. The fingerprint sensor 142 may be an area sensor, meaning that the fingerprint sensor 142 does not require a swipe of the user's finger to capture enough of a fingerprint to uniquely identify the user. The fingerprint sensor 142 may have a sufficiently high resolution such that it can be used to uniquely identify an individual using a relatively small section of the user's fingerprint. In some cases, the input surface has a width between 2 mm and 5 mm, and the fingerprint sensor 142 can still uniquely identify an individual using a fingerprint captured at the input surface. In some cases, the fingerprint sensor 142 may be a swipe-style fingerprint sensor.

Outputs provided by the electronic device 100 may be responsive to fingerprint inputs detected using the fingerprint sensor 142. For example, graphical outputs provided by the display 122 and/or audio outputs provided by an audio output device may be responsive to fingerprint inputs detected using the fingerprint sensor 142.

The translation sensor 144 can be any suitable device for detecting translational inputs at the modular sensing assembly 110. As used herein, "translational inputs" may refer to inputs to the modular sensing assembly 110 that cause the modular sensing assembly or a portion thereof to move or translate. Translation may include inward and outward translation, lateral translation, and other movement of one or more components of the modular sensing assembly 110 (e.g., the cover). For example, the cover of the modular sensing assembly 110 may depress in response to a user pressing on the input surface. The modular sensing assembly 110 or a portion thereof may translate inward in response to the user pressing on the input surface. The translation sensor 144 may detect this as a translational input.

The translation sensor 144 may be implemented as a physical switch (e.g., a tactile dome switch), a capacitive sensor, a resistive sensor, a contact sensor, a magnetic sensor, an optical sensor, an ultrasonic sensor, so on. The translation sensor 144 may provide a signal in response to a translational input that may indicate that the translational input occurs, where an input occurs, and/or a measure of the input (e.g., a force measurement). In some cases, the translation sensor 144 may be positioned beneath the cover of the modular sensing assembly 110 to detect translational inputs on or near the input surface.

Outputs provided by the electronic device 100 may be responsive to translational inputs detected using the translation sensor 144. For example, graphical outputs provided by the display 122 and/or audio outputs provided by an audio output device may be responsive to translational inputs detected using the translation sensor 144.

The audio sensor 146 can be any suitable device for detecting audio inputs at the modular sensing assembly 110. As used herein, "audio inputs" may refer to any detected or measured sounds. For example, the audio sensor 146 may detect sounds from the environment surrounding the electronic device 100 for voice commands and other device control, recording, noise-level detection, voice communication (e.g., phone calls), and the like.

The audio sensor 146 may be implemented as a microphone or any device for measuring or detecting audio signals. The audio sensor 146 may provide a signal corresponding to the audio input to the processing unit 128. In some cases, the audio sensor 146 may be positioned beneath the cover of the modular sensing assembly 110 to detect audio inputs through the cover and/or through an opening in the cover.

Outputs provided by the electronic device 100 may be responsive to audio inputs detected using the audio sensor 146. For example, graphical outputs provided by the display 122 and/or audio outputs provided by an audio output device may be responsive to audio inputs detected using the audio sensor 146.

The ECG electrode 148 may be disposed on one or more exterior surfaces of the modular sensing assembly 110. The processing unit 128 or other sensing circuitry of the electronic device 100 may monitor for voltages or signals received on the ECG electrode 148. The electronic device 100 may include one or more additional electrodes positioned on exterior surfaces of the electronic device that may be used to provide an electrocardiogram function for the electronic device.

In some embodiments, the ECG electrode 148 may be disposed (e.g., PVD deposited) on an exterior surface of the modular sensing assembly 110. The ECG electrode 148 may be positioned on an exterior surface of the cover of the modular sensing assembly 110. The surface may be any transparent, semi-transparent, translucent, or opaque surface made out of an amorphous solid, glass, a crystal or crystalline material (such as sapphire or zirconia), plastic, or the like. The ECG electrode 148 may be positioned along a portion of the perimeter of a cover of the modular sensing assembly (e.g., a cover that forms an input surface). The portion of the perimeter of the cover may be curved, and the ECG electrode 148 may conform to a curvature of the perimeter of the cover. As an example, the portion of the perimeter of the cover along which the ECG electrode 148 is placed may define a 180-degree curve. The ECG electrode 148 may at least partially surround a region of the cover that does not include the ECG electrode. The ECG electrode 148 may have a C or U shape and may at least partially surround a portion of the cover where the ECG electrode is not present. The ECG electrode 148 may extend from the exterior surface of the cover, around an edge of the cover, to a connector beneath the cover (e.g., a connector coupled to an interior surface of the cover). This may improve the ability of the modular sensing assembly 110 to exclude contaminants by obviating a need to pass a connector through a hole in the cover or another component of the electronic device 100.

Outputs provided by the electronic device 100 may be responsive to signals received on the ECG electrode 148. For example, graphical outputs provided by the display 122 and/or audio outputs provided by an audio output device may be responsive to signals received on the ECG electrode 148.

The output device(s) 149 may provide outputs at the modular sensing assembly 110. The output devices 149 may include a haptic output device (e.g., a haptic actuator) for providing haptic outputs, an audio output device (e.g., a speaker) for providing audio outputs, and/or a visual output device (e.g., lights) for providing visual outputs.

As used herein, the terms "haptic output" and "tactile output" may refer to outputs produced by the electronic device that may be perceived through user touch. Examples of haptic outputs include vibrations, deflections, and other movements of a device housing, a device cover, or input device, or another device component that forms an input surface of the electronic device. In some cases, haptic outputs may provide feedback regarding inputs received at particular locations of the electronic device. For example, haptic outputs may be provided at the modular sensing assembly 110 to provide feedback related to an input provided at the modular sensing assembly. In other cases, haptic outputs may provide other types of feedback or information to users, such as alerts received at the electronic device.

The modular sensing assembly 110 may include more or fewer components than those shown and described with respect to FIG. 1B. In some cases, a single device or sub-assembly may provide functionality described with respect to multiple components above. For example, a single audio device may be capable of detecting audio inputs and providing audio inputs. As another example, a single sensing device may be capable of detecting touch inputs and fingerprint inputs. Similarly, a single sensing device may be capable of detecting touch inputs and translational inputs.

Figure 2A:
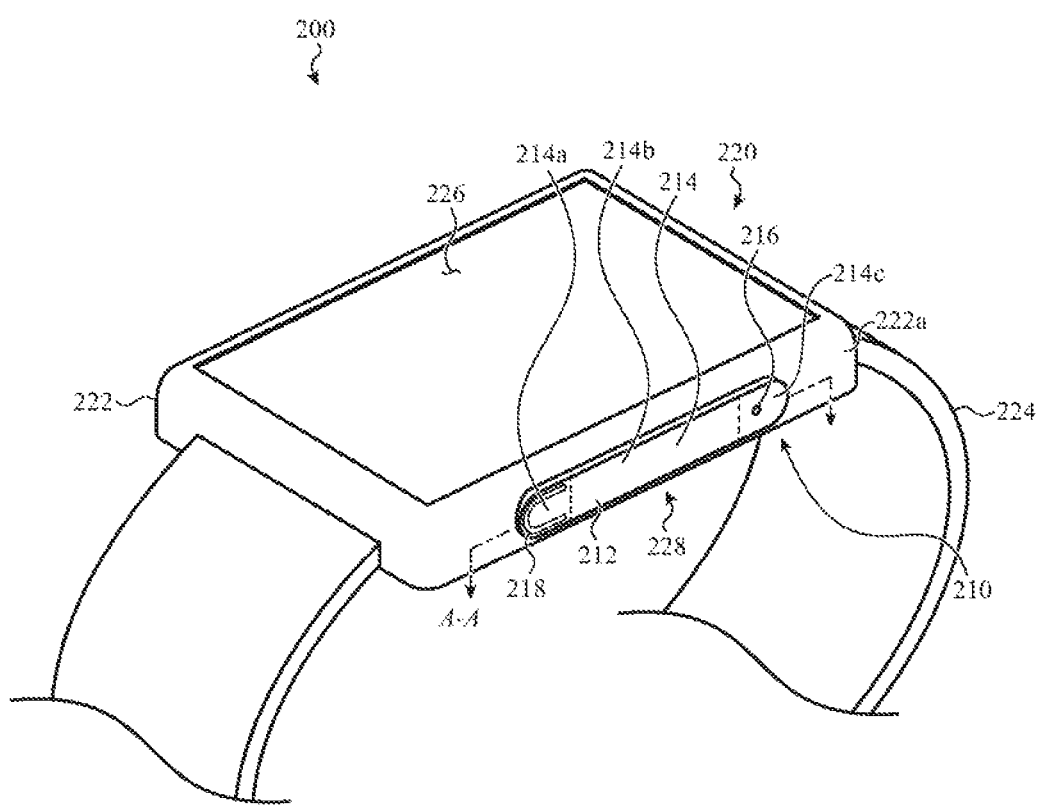
FIGS. 2A-2C illustrate an example electronic watch that includes a modular sensing assembly.
Figure 2B:
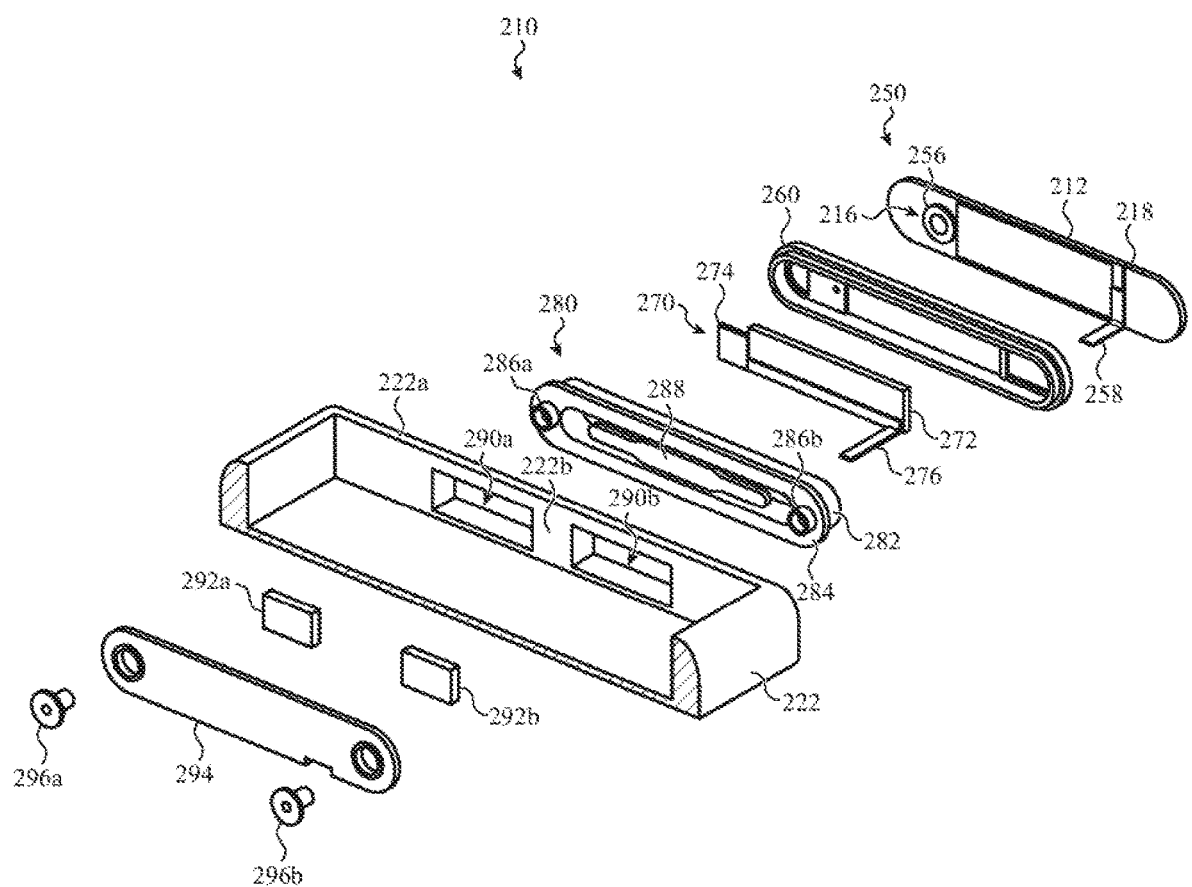
Figure 2C:
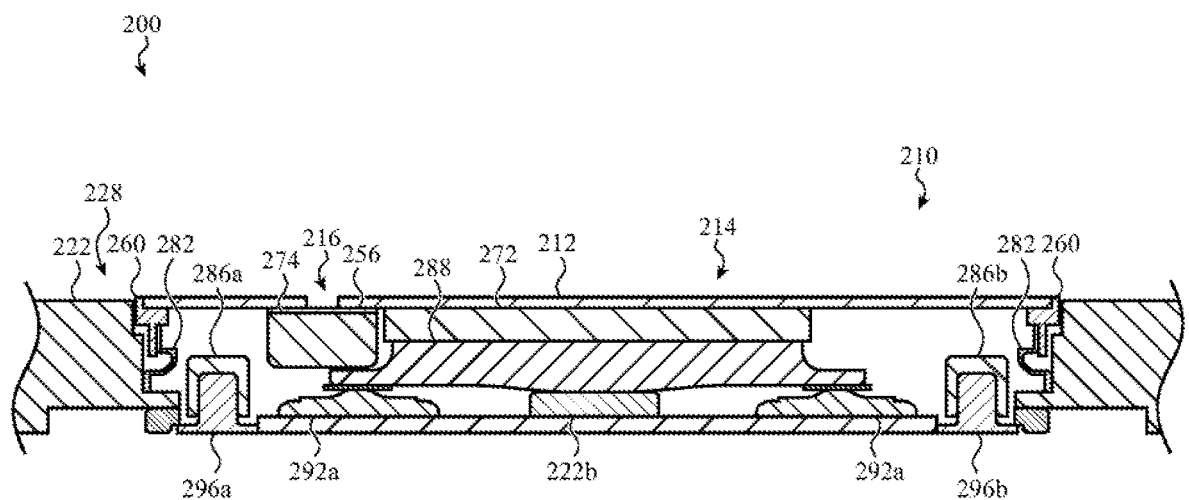

FIGS. 2A-2C illustrate an example electronic watch 200 that includes a modular sensing assembly 210. The electronic watch 200 may have the same or similar functionality and structure as the electronic device 100 discussed with respect to FIGS. 1A and 1B. Other devices that may incorporate the modular sensing assemblies described herein include other wearable electronic devices, other timekeeping devices, other health monitoring or fitness devices, other portable computing devices, mobile phones (including smart phones), tablet computing devices, digital media players, virtual reality devices, audio devices (including earbuds and headphones), and the like.

As shown in FIG. 2A, the electronic watch 200 may include a watch body 220 and a watch band 224. The watch body 220 may include a housing 222. The housing 222 may contain one or more components of the electronic watch 200 and may define at least part of an external surface of the electronic watch.

The modular sensing assembly 210 may be positioned in a recess 228 along a sidewall 222a of the housing 222. The modular sensing assembly 210 may include a cover 212 that defines at least a portion of an input surface 214 that forms part of an exterior surface of the electronic watch 200. The input surface 214 may include multiple regions for detecting different types of inputs. For example, as shown in FIG. 2A, the input surface 214 may include an ECG region 214a where ECG signals may be detected, a fingerprint-sensing region 214b where fingerprint inputs may be detected, and an audio sensing region 214c that includes an opening 216 through which audio signals may be detected. In some cases, the ECG region 214a, the fingerprint-sensing region 214b, and/or the audio sensing region 214c may also be a touch-sensing region in which touch inputs may be received.

The modular sensing assembly 210 may be capable of receiving translational inputs. For example, a user may press inward on the input surface 214 to provide a translational input to the modular sensing assembly 210. The cover 212 may translate inward in response to the translational input. In some cases, the cover 212 may deflect or bend in response to the translational input. In some cases, the cover 212 may not translate, deflect, or bend in response to a translational input. The modular sensing assembly 210 may include one or more translation sensors to detect the translational inputs.

The ECG region 214a may include an ECG electrode 218 disposed on an exterior surface of the cover 212. The ECG electrode 218 may be configured to detect ECG signals, for example from a user's finger placed on the ECG electrode. The ECG signals may be used to provide an electrocardiogram function for the electronic watch 200. As shown in FIG. 2A, the ECG electrode 218 may be positioned along a portion of the perimeter of the cover 212. The portion of the perimeter of the cover 212 may be curved, and the ECG electrode 218 may conform to a curvature of the perimeter of the cover 212. As an example, the portion of the perimeter of the cover 212 along which the ECG electrode 218 is placed may define a 180-degree curve as shown in FIG. 2A. The ECG electrode 218 may at least partially surround a region of the exterior cover that does not include the ECG electrode. For example, as shown in FIG. 2A, the ECG electrode 218 has a C or U shape and at least partially surrounds a portion of the ECG region 214a where the ECG electrode is not present. As discussed in more detail below, the ECG electrode 218 may extend from the exterior surface of the cover 212, around an edge of the cover, to a connector beneath the cover (e.g., a connector coupled to an interior surface of the cover). This may improve the ability of the modular sensing assembly 210 to exclude contaminants by obviating a need to pass a connector through a hole in the cover 212 or another component of the electronic watch 200.

The ECG electrode 218 may be formed of any suitable material or combination of materials for receiving ECG signals, including metals and other conductive materials. The cover 212 or one or more portions thereof may be formed of a non-conductive material to electrically isolate the ECG electrode 218 from other components of the electronic watch 200 to reduce interference and signal noise being introduced into the ECG signals. In some cases, the modular sensing assembly 210 may include an isolating component disposed between the ECG electrode 218 and one or more additional components of the modular sensing assembly to reduce interference and signal noise being introduced into the ECG signals.

The cover 212 may be configured to allow inputs to be detected by components of the modular sensing assembly 210 that are positioned beneath the cover. The cover 212 may be formed of or include non-conductive and/or dielectric materials that allow sensing signals, such as capacitive signals, ultrasonic signals, and the like to pass through the cover. As an example, the cover 212 may be formed of sapphire. The cover 212 may be formed of a transparent or translucent material to allow optical sensing signals to pass through the cover. In some cases, structural features of the cover 212 allow signals to pass through the cover. For example, the cover may include openings that allow sensing signals (e.g., optical signals) to pass through the cover.

In some cases, the electronic watch 200 may include a display cover 226 facing away from a user's skin as the watch 200 is worn. In some cases, the display cover 226 is mounted to or coupled to the housing 222. The display cover 226 may be positioned over and protect a display mounted within the housing 222 (e.g., display 122 of FIG. 1A). The display may be viewable by a user through the display cover 226. In some cases, the display cover 226 may be part of a display stack, which may include touch sensing or force sensing capability. The display may be configured to depict a graphical output of the electronic watch 200, and a user may interact with the graphical output (e.g., using a finger, stylus, or other pointer). As one example, the user may select (or otherwise interact with) a graphic, icon, or the like presented on the display by touching or pressing (e.g., providing touch input) on the display at the location of the graphic. In some cases, the haptic outputs provided by the haptic device correspond to the graphical output of the display and/or inputs received via the display.

As used herein, the term "display cover" may be used to refer to any transparent, semi-transparent, or translucent surface made out of glass, a crystalline material (such as sapphire or zirconia), plastic, or the like. Thus, it should be appreciated that the term "display cover," as used herein, encompasses amorphous solids as well as crystalline solids. In some examples, the display cover 226 may be a sapphire cover. The display cover 226 may also be formed of glass, plastic, or other materials.

The watch band 224 may be used to secure the electronic watch 200 to a user, another device, a retaining mechanism, and so on. The housing 222 may include structures for attaching the watch band 224 to the watch body 220. In some cases, the structures may include elongate recesses or openings through which ends of the watch band 224 may be inserted and attached to the watch body 220. In other cases (not shown), the structures may include indents (e.g., dimples or depressions) in the housing 222, which indents may receive ends of spring pins that are attached to or threaded through ends of a watch band to attach the watch band to the watch body.

FIG. 2B illustrates a partial exploded view of the example electronic watch 200. FIG. 2B shows example components of the modular sensing assembly 210 and a cutaway portion of the housing 222. The modular sensing assembly 210 may include a cover sub-assembly 250, a trim member 260, a sensing sub-assembly 270, a button sub-assembly 280, translation sensors 292a, 292b, and a retention bracket 294. The components of the modular sensing assembly 210 may be coupled together and/or coupled to the housing 222 using one or more fasteners (e.g., fasteners 296a, 296b).

The modular sensing assembly 210 may be disposed in a recess along the sidewall 222a of the housing 222, as described in more detail with respect to FIG. 2C below. The sidewall 222a may define one or more passages 290a, 290b that extend through the sidewall and into the interior volume of the electronic watch 200. The passages 290a, 290b may facilitate attachment of the modular sensing assembly 210 to the housing 222, as described in more detail with respect to FIG. 2C below. Additionally, the passages 290a, 290b may facilitate the transmission of signals from the modular sensing assembly into the interior volume of the electronic watch 200 (e.g., using connectors that operably couple the components of the modular sensing assembly 210 to a processing unit or other circuitry of the electronic watch 200).

As shown in FIG. 2B, the cover 212 of the modular sensing assembly 210 may be part of a cover sub-assembly that includes a membrane 256, the ECG electrode 218, and an ECG connector 258. The ECG electrode 218 may extend from the exterior surface of the cover 212, around an edge of the cover, to the connector 258 beneath the cover. The connector 258 may be coupled to an interior surface of the cover 212, and may extend through a passage 290a, 290b into the interior volume of the electronic watch 200 (e.g., to a processing unit or other circuitry of the electronic watch 200). This may give the ECG signal from the ECG electrode 218 a clear signal path to a processing unit while electrically isolating the signal from the housing and the touch sensor. The ECG electrode 218 and associated circuitry may be shielded from, operate on a different frequency from, or otherwise be configured to reduce parasitic effects with the touch sensor 272 and/or other components of the modular sensing assembly 210.

The sensing sub-assembly 270 may be positioned beneath the cover 212, and may include a touch sensor 272 and an audio sensor 274. The touch sensor 272 may detect touch inputs on the input surface 214 of the cover 212. As discussed above with respect to FIG. 1B, the touch sensor 272 may be implemented as a capacitive sensor, a resistive sensor, a contact sensor, a magnetic sensor, an optical sensor, an ultrasonic sensor, and so on. In some cases, the touch sensor 272 is also a fingerprint sensor for detecting fingerprint inputs on the input surface 214. For example, the touch sensor 272 may be a capacitive sensor configured to detect touch inputs and fingerprint inputs on the input surface. The fingerprint sensor may be implemented as a capacitive sensor, a resistive sensor, a contact sensor, a magnetic sensor, an optical sensor, an ultrasonic sensor, a camera, and so on. In some cases, the modular sensing assembly 210 may include a touch sensor and a fingerprint sensor that are separate components.

The audio sensor 274 may be positioned beneath an opening 216 in the cover 212, and may be configured to detect audio inputs. The membrane 256 may be positioned beneath the opening 216 in the cover 212 to prevent the ingress of contaminants into the modular button assembly and/or the interior volume of the electronic watch 200 via the opening 216. The membrane may be at least partially transmissive to sound waves so that the audio sensor 274 can detect audio inputs. The membrane 256 may be formed of any suitable material that is at least partially transmissive to sound waves and that forms a barrier to exclude contaminants.

The sensing sub-assembly 270 may also include one or more connectors 276 that operably couple the touch sensor 272 and the audio sensor 274 to a processing unit or other circuitry of the electronic watch 200. The connector 276 may extend through a passage 290a, 290b into the interior volume of the electronic watch 200.

The trim member 260 may extend at least partially around a perimeter of the cover 212, and may at least partially surround the cover 212, the touch sensor 272, and the audio sensor 274. As discussed in more detail below, the trim member 260 may form part of an assembly enclosure of the modular sensing assembly.

The button sub-assembly 280 may include a sealing member 282, a button retainer 284, and a button member 288. The button member 288 may be positioned within an opening formed by the sealing member 282 and/or the button retainer 284. The button retainer 284 may at least partially surround the button member 288, and the sealing member 282 may extend around the button retainer 284. As described in more detail below with respect to FIG. 2C, the button member 288 may transfer forces applied to the cover 212 to the translation sensors 292a, 292b to recognize translational inputs.

The sealing member 282 may be a compressible gasket that forms a seal between the housing 222 and the modular sensing assembly 210. For example, as shown in FIG. 2C, the sealing member 282 may be positioned along an inside surface of the recess 228. The sealing member 282 may extend around one or more passages 290a, 290b into the interior volume to prevent contaminants from entering the interior volume via the passages. The sealing member 282 may have a shape that allows it to compress or otherwise deform in response to translation of the cover 212, trim member 260, or other components of the modular sensing assembly 210. In some cases, the sealing member 282 is co-molded with the button retainer 284 to simplify the assembly process of the modular sensing assembly 210.

The translation sensors 292a, 292b may be configured as any suitable devices for detecting translational inputs at the modular sensing assembly 210. Each translation sensor 292a, 292b may be implemented as a physical switch (e.g., a tactile dome switch), a capacitive sensor, a resistive sensor, a contact sensor, a magnetic sensor, an optical sensor, an ultrasonic sensor, so on. The translation sensors 292a, 292b may provide signals in response to translational inputs that may indicate that the translational input occurs, where an input occurs, and/or a measure of the input (e.g., a force measurement).

The retention bracket 294 may be positioned along an interior surface of the sidewall 222a. The retention bracket 294, along with fasteners 296a, 296b may be used to couple together the components of the modular sensing assembly 210. The button retainer 284 may include coupling mechanisms that allow the fasteners to couple the button sub-assembly 280 to the retention bracket 294. For example, the button retainer 284 may include female threaded connectors 286a, 286b configured to interface with threads of the fasteners 296a, 296b.

The retention bracket 294 and the fasteners 296a, 296b may be used to secure the modular sensing assembly 210 to the housing 222. Coupling the retention bracket 294 to the button retainer 284 may secure the modular sensing assembly 210 to the housing 222.

In some cases, the modular sensing assembly 210 may include an assembly enclosure formed by one or more components. The assembly enclosure may at least partially surround and/or enclose various components of the modular sensing assembly 210, and allow the modular sensing assembly 210 to reduce the number of necessary sealing members. For example, the components of the sensing sub-assembly may be at least partially surrounded by the assembly enclosure. The assembly enclosure may be formed by one or more of the cover 212, the trim member 260, the sealing member 282, the button retainer 284, and the retention bracket 294.

FIG. 2C illustrates a cross-section view of the example electronic watch 200 of FIG. 2A, taken through section line A-A. As noted above, the modular sensing assembly 210 may be disposed in a recess 228 along the sidewall 222a of the housing 222.

The modular sensing assembly 210 may receive translational inputs that cause the cover 212 to translate or otherwise move. Turning to FIG. 2C, a translational input applied to the input surface 214 may cause the cover 212 to translate downward toward the translation sensor 292a, 292b. The button member 288 may be positioned between the cover 212 and the translation sensors 292a, 292b, and may be configured to translate in response to a translational input on the input surface that causes the cover 212 to translate. The button member 288 may transfer forces applied to the cover 212 to the translation sensors 292a, 292b to recognize translational inputs.

Translation of the button member 288 may actuate one or both of the translation sensors 292a, 292b. In some cases, the button member 288 may be moved in a rocking motion to depress one of the translation sensors 292a, 292b based on a location of the translational input. For example, a translational input on a first region of the cover 212 (e.g., a left side of the cover with respect to FIG. 2C) may cause a first end (e.g., the left end) of the button member to depress, thereby actuating the translation sensor 292a. Similarly, a translational input on a second region of the cover 212 (e.g., a right side of the cover with respect to FIG. 2C) may cause a second end (e.g., the right end) of the button member to depress, thereby actuating the translation sensor 292b. The button member 288 may be positioned along a portion 222b of the housing or another component of the electronic watch 200 to facilitate the rocking motion of the button member.

The passages 290a, 290b may facilitate attachment of the modular sensing assembly 210 to the housing 222. For example, the retention bracket 294 may be positioned along an interior surface of the sidewall 222a, and the fasteners 296a, 296b may pass through the passages 290a, 290b and couple the other components of the modular sensing assembly 210 to the retention bracket 294. Coupling the components of the modular sensing assembly 210 to the retention bracket 294 may secure the modular sensing assembly 210 to the housing 222.

Figure 3A:
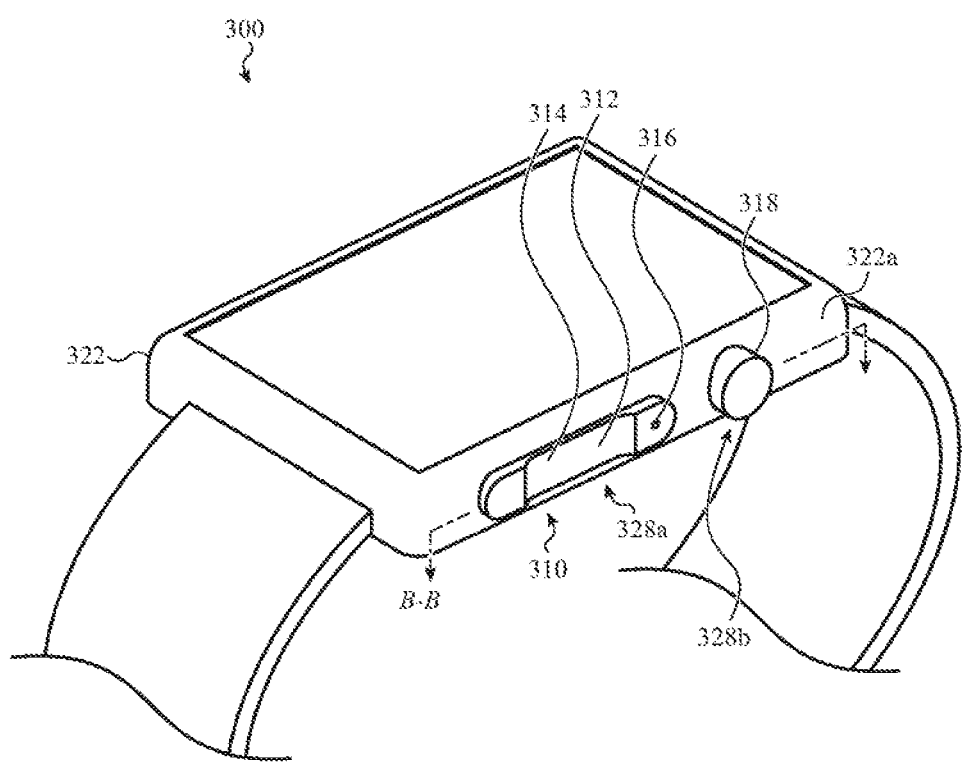
FIGS. 3A-3C illustrate an example electronic watch that includes a modular sensing assembly.
Figure 3B:
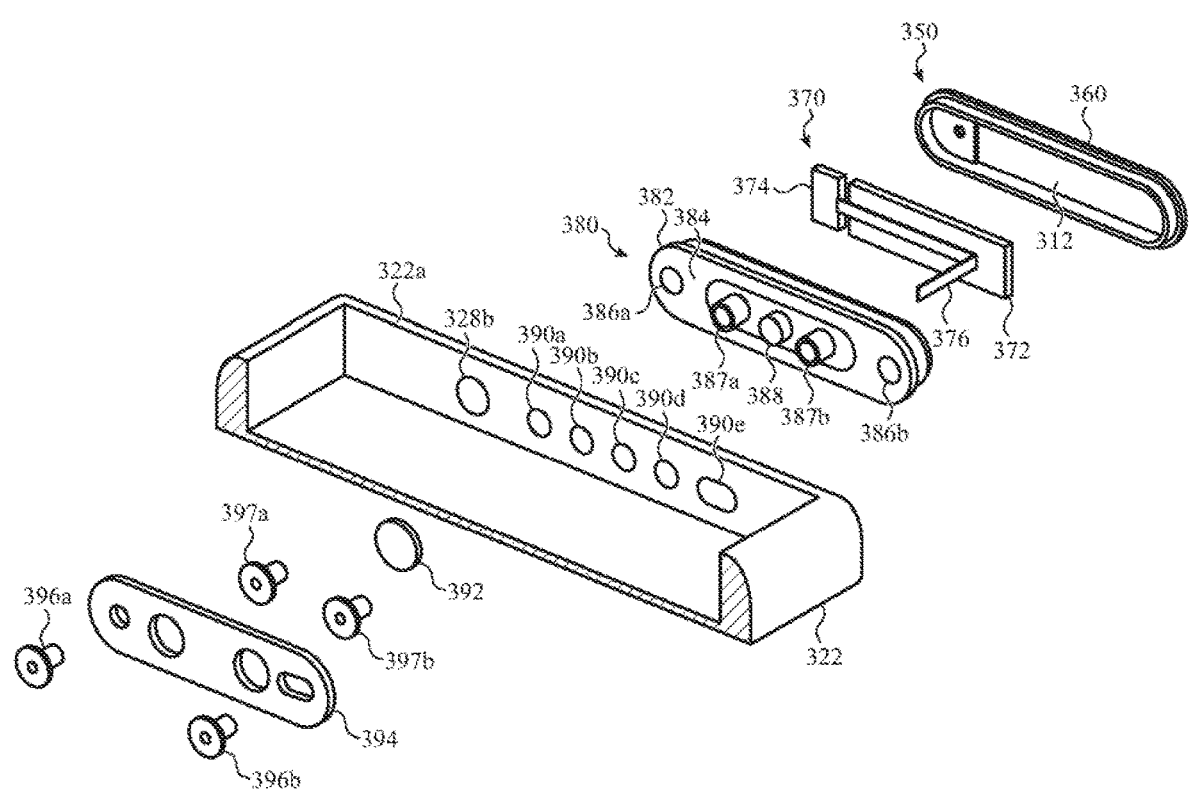
Figure 3C:
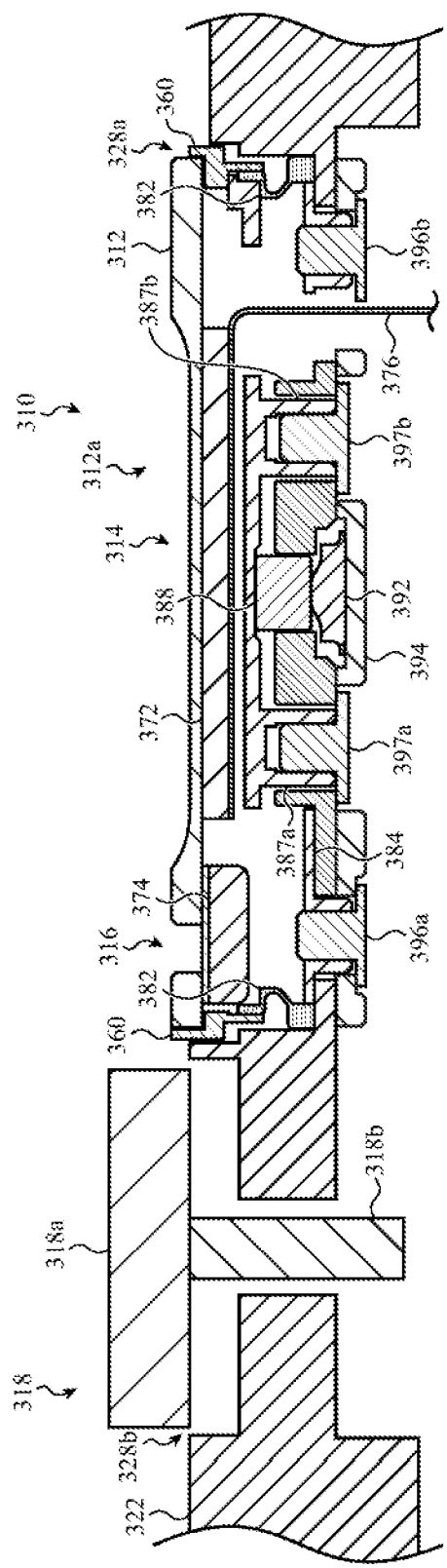

FIGS. 3A-3C illustrate an example electronic watch 300 that includes a modular sensing assembly 310. The example electronic watch 300 may be similar to other electronic devices discussed herein (e.g., electronic devices 100, 200), and may include similar structure and/or functionality. As shown in FIG. 3A, the electronic watch 300 may include a modular sensing assembly 310 positioned in a recess 328a along a sidewall 322a of a housing 322. The modular sensing assembly 310 may include a cover 312 that defines at least a portion of an input surface 314 that forms part of an exterior surface of the electronic watch 300. The cover 316 may include an opening, for example for use in detecting audio inputs.

The electronic watch 300 may include at least one input device or selection device, such as a crown, scroll wheel, knob, dial, button, or the like, which may be operated by a user of the electronic watch. The electronic watch 300 may include a crown 318 positioned along the sidewall 322a. The crown 318 may be configured to receive rotational inputs and/or translational inputs. A graphical output of a display of the electronic watch 300 may be responsive to inputs received at the crown 318 and/or the modular sensing assembly 310.

FIG. 3B illustrates a partial exploded view of the example electronic watch 300. FIG. 3B shows example components of the modular sensing assembly 310 and a cutaway portion of the housing 322. The modular sensing assembly 310 may include a cover sub-assembly 350, a sensing sub-assembly 370, a button sub-assembly 380, a translation sensor 392, and a retention bracket 394. The components of the modular sensing assembly 310 may be coupled together and/or coupled to the housing 322 using fasteners 396a, 396b and 397a, 397b.

The cover sub-assembly may include the cover 312 and a trim member 360. The sensing sub-assembly 370 may include a touch sensor 372, an audio sensor 374, and a connector 376. The button sub-assembly 380 may include a sealing member 382, a button retainer 384, and a button member 388.

The button member 388 may be movably coupled to the housing 322 such that the button member 388 may translate in response to a translational input to the cover 312. The button member may be aligned with a passage 390c in the sidewall 322a that is aligned with the translation sensor 392. As the button member 388 translates in response to a translational input, it may actuate the translation sensor 392. In some cases, the components of the modular sensing assembly 310 do not move in response to a translational input, and the translation sensor 392 detects a force applied to the cover 312.

FIG. 3C illustrates a cross-section view of the example electronic watch 300 of FIG. 3A, taken through section line B-B. As noted above, the modular sensing assembly 310 may be disposed in a recess 328a along the sidewall 322a of the housing 322.

As shown in FIG. 3C, the cover 312 may include a recessed region 312a that may guide a user's finger to an appropriate portion of the input surface 314 to provide one or more inputs. For example, the recessed region 312a may align a user's finger with a fingerprint sensor (e.g., a fingerprint sensor of the touch sensor 372).

As shown in FIG. 3C, the crown 318 may include that includes a crown body 318a and a shaft 318b. The housing 322 may define a passage 328b through which the shaft extends from an exterior surface of the sidewall 322a and into the interior volume. The crown body 318a may be attached and/or coupled to the shaft, and may be accessible to a user exterior to the housing 322.

The crown body 318a may be user-rotatable, and may be manipulated (e.g., rotated, pressed) by a user to rotate or translate the shaft 318b. The shaft 318b may be mechanically, electrically, magnetically, and/or optically coupled to components within the housing 322. A user's manipulation of the crown body 318a and shaft 318b may be used, in turn, to manipulate or select various elements displayed on the display, to adjust a volume of a speaker, to turn the watch 300 on or off, and so on. The crown body 318a may be operably coupled to a circuit within the housing 322 (e.g., a processing unit), but electrically isolated from the housing 322. The crown 318 may include a conductive electrode used to measure an ECG or other health-related measurement.

The retention bracket 394 may be positioned along an interior surface of the sidewall 322a. The retention bracket 394, along with fasteners 396a, 396b may be used to couple together the components of the modular sensing assembly 310. The button retainer 384 may include coupling mechanisms for coupling the button sub-assembly 380 to the retention bracket 394 using fasteners 396a, 396b. For example, the button retainer 384 may include female threaded connectors 386a, 386b configured to interface with threads of the fasteners 396a, 396b through passages 390a, 390e. The button member 388 may include coupling mechanisms for coupling the button member 388 to the housing 322. For example, the button member 388 may include female threaded connectors 387a, 387b configured to interface with threads of the fasteners 397a, 397b through passages 390b, 390d.

The retention bracket 394 and the fasteners 396a, 396b may be used to secure the modular sensing assembly 310 to the housing 322. Coupling the retention bracket 394 to the button retainer 384 may secure the modular sensing assembly 310 to the housing 322.

Figure 4:
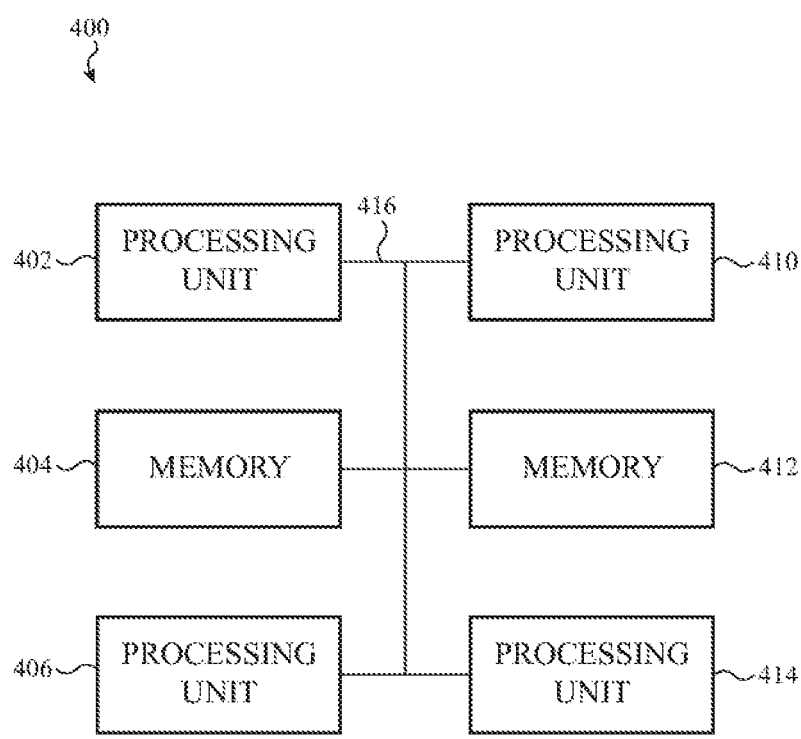
FIG. 4 illustrates a sample electrical block diagram of an electronic device that may incorporate a modular sensing assembly.

FIG. 4 illustrates a sample electrical block diagram of an electronic device 400 that may incorporate a modular sensing assembly. The electronic device may in some cases take the form of any of the electronic devices described with reference to FIGS. 1A-3C, or other portable or wearable electronic devices. The electronic device 400 can include a display 412 (e.g., a light-emitting display), a processing unit 402, a power source 414, a memory 404 or storage device, an input device 406 (e.g., a modular sensing assembly), and an output device 410.

The processing unit 402 can control some or all of the operations of the electronic device 400. The processing unit 402 can communicate, either directly or indirectly, with some or all of the components of the electronic device 400. For example, a system bus or other communication mechanism 416 can provide communication between the processing unit 402, the power source 414, the memory 404, the input device(s) 406, and the output device(s) 410.

The processing unit 402 can be implemented as any electronic device capable of processing, receiving, or transmitting data or instructions. For example, the processing unit 402 can be a microprocessor, a central processing unit (CPU), an application-specific integrated circuit (ASIC), a digital signal processor (DSP), or combinations of such devices. As described herein, the term "processing unit" is meant to encompass a single processor or processing unit, multiple processors, multiple processing units, or other suitably configured computing element or elements.

It should be noted that the components of the electronic device 400 can be controlled by multiple processing units. For example, select components of the electronic device 400 (e.g., an input device 406) may be controlled by a first processing unit and other components of the electronic device 400 (e.g., the display 412) may be controlled by a second processing unit, where the first and second processing units may or may not be in communication with each other. In some cases, the processing unit 402 may determine a biological parameter of a user of the electronic device, such as an ECG for the user.

The power source 414 can be implemented with any device capable of providing energy to the electronic device 400. For example, the power source 414 may be one or more batteries or rechargeable batteries. Additionally or alternatively, the power source 414 can be a power connector or power cord that connects the electronic device 400 to another power source, such as a wall outlet.

The memory 404 can store electronic data that can be used by the electronic device 400. For example, the memory 404 can store electrical data or content such as, for example, audio and video files, documents and applications, device settings and user preferences, timing signals, control signals, and data structures or databases. The memory 404 can be configured as any type of memory. By way of example only, the memory 404 can be implemented as random access memory, read-only memory, Flash memory, removable memory, other types of storage elements, or combinations of such devices.

In various embodiments, the display 412 provides a graphical output, for example associated with an operating system, user interface, and/or applications of the electronic device 400. In one embodiment, the display 412 includes one or more sensors and is configured as a touch-sensitive (e.g., single-touch, multi-touch) and/or force-sensitive display to receive inputs from a user. For example, the display 412 may be integrated with a touch sensor (e.g., a capacitive touch sensor) and/or a force sensor to provide a touch-and/or force-sensitive display. The display 412 is operably coupled to the processing unit 402 of the electronic device 400.

The display 412 can be implemented with any suitable technology, including, but not limited to liquid crystal display (LCD) technology, light emitting diode (LED) technology, organic light-emitting display (OLED) technology, organic electroluminescence (OEL) technology, or another type of display technology. In some cases, the display 412 is positioned beneath and viewable through a cover that forms at least a portion of an enclosure of the electronic device 400.

In various embodiments, the input devices 406 may include any suitable components for detecting inputs. Examples of input devices 406 include audio sensors (e.g., microphones), optical or visual sensors (e.g., cameras, visible light sensors, or invisible light sensors), proximity sensors, touch sensors, force sensors, mechanical devices (e.g., crowns, switches, buttons, or keys), vibration sensors, orientation sensors, motion sensors (e.g., accelerometers or velocity sensors), location sensors (e.g., global positioning system (GPS) devices), thermal sensors, communication devices (e.g., wired or wireless communication devices), resistive sensors, magnetic sensors, electroactive polymers (EAPs), strain gauges, electrodes, and so on, or some combination thereof. Each input device 406 may be configured to detect one or more particular types of input and provide a signal (e.g., an input signal) corresponding to the detected input. The signal may be provided, for example, to the processing unit 402.

As discussed above, in some cases, the input device(s) 406 include a touch sensor (e.g., a capacitive touch sensor) integrated with the display 412 to provide a touch-sensitive display. Similarly, in some cases, the input device(s) 406 include a force sensor (e.g., a capacitive force sensor) integrated with the display 412 to provide a force-sensitive display.

The output devices 410 may include any suitable components for providing outputs. Examples of output devices 410 include audio output devices (e.g., speakers), visual output devices (e.g., lights or displays), tactile output devices (e.g., haptic output devices), communication devices (e.g., wired or wireless communication devices), and so on, or some combination thereof. Each output device 410 may be configured to receive one or more signals (e.g., an output signal provided by the processing unit 402) and provide an output corresponding to the signal.

In some cases, input devices 406 and output devices 410 are implemented together as a single device. For example, an input/output device or port can transmit electronic signals via a communications network, such as a wireless and/or wired network connection. Examples of wireless and wired network connections include, but are not limited to, cellular, Wi-Fi, Bluetooth, IR, and Ethernet connections.

The processing unit 402 may be operably coupled to the input devices 406 and the output devices 410. The processing unit 402 may be adapted to exchange signals with the input devices 406 and the output devices 410. For example, the processing unit 402 may receive an input signal from an input device 406 that corresponds to an input detected by the input device 406. The processing unit 402 may interpret the received input signal to determine whether to provide and/or change one or more outputs in response to the input signal. The processing unit 402 may then send an output signal to one or more of the output devices 410, to provide and/or change outputs as appropriate.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. An electronic watch comprising:
   a housing defining an interior volume and having a sidewall and a recess formed in the sidewall;
   a processing unit positioned within the interior volume;
   a display operably coupled to the processing unit; and
   a modular sensing assembly disposed in the recess and operably coupled to the processing unit, the modular sensing assembly comprising:
     an assembly enclosure comprising:
       a cover defining a portion of an exterior surface of the electronic watch; and
       a trim member extending around a perimeter of the cover;
     an electrocardiograph electrode disposed on the cover and configured to detect an electrocardiograph signal;
     a sensing sub-assembly positioned between the cover and the sidewall and at least partially surrounded by the trim member, the sensing sub-assembly comprising:
       a touch sensor configured to detect a touch input on the cover;
       an audio sensor configured to detect an audio input;
       a translation sensor positioned beneath the cover and configured to detect a translational input to the cover; and
     a sealing member positioned between the trim member and the housing and configured to exclude contaminants from the interior volume; wherein:
   the display is configured to provide a graphical output that is responsive to the electrocardiograph signal, the touch input, the audio input, and the translational input.

2. The electronic watch of claim 1, wherein:
   the sidewall further defines a passage that extends through the sidewall to the interior volume;
   the modular sensing assembly further comprises:
     a retention bracket positioned along an interior surface of the sidewall;
     a button member positioned beneath the cover and configured to depress in response to the translational input, thereby actuating the translation sensor; and
     a button retainer at least partially surrounding the button member and coupled to the retention bracket via a fastener that extends through the passage; and
   the sealing member extends around the button retainer.

3. The electronic watch of claim 2, wherein:
   the translation sensor is a first translation sensor positioned beneath a first end of the button member;
   the modular sensing assembly further comprises a second translation sensor positioned beneath a second end of the button member;
   a first translational input on a first region of the cover causes the first end of the button member to depress, thereby actuating the first translation sensor; and
   a second translational input on a second region of the cover causes the second end of the button member to depress, thereby actuating the second translation sensor.

4. The electronic watch of claim 3, wherein:
   the passage is a first passage;
   the sidewall further defines a second passage that extends through the sidewall to the interior volume;
   the first translation sensor is positioned at least partially within the first passage; and
   the second translation sensor is positioned at least partially within the second passage.

5. The electronic watch of claim 1, wherein the touch sensor is a capacitive touch sensor and is further configured to detect a fingerprint input.

6. The electronic watch of claim 1, wherein the cover comprises sapphire.

7. The electronic watch of claim 1, wherein:
   the cover defines an opening extending through the cover; and
   the audio sensor is positioned beneath the opening and configured to detect the audio input through the opening.

8. The electronic watch of claim 7, wherein the electronic watch further comprises a membrane positioned beneath the opening and configured to prevent the contaminants from passing through the opening.

9. An electronic watch comprising:
   a display;
   a processing unit operably coupled to the display;
   a housing at least partially surrounding the display, the housing having a sidewall and defining a recess formed in the sidewall; and
   a modular sensing assembly disposed in the recess, and comprising:
     a cover defining an input surface;

a capacitive sensor positioned beneath the input surface and configured to:
    detect a touch input on the input surface; and
    detect a fingerprint input on the input surface;
an audio sensor positioned beneath the cover and configured to detect an audio input through an opening in the cover;
a translation sensor positioned beneath the cover and configured to detect a translational input at the input surface; and
a trim member at least partially surrounding the cover, the capacitive sensor, and the audio sensor; wherein:
the display is configured to provide a graphical output that is responsive to the touch input, the fingerprint input, the audio input, and the translational input.

10. The electronic watch of claim 9, wherein:
the electronic watch further comprises a crown positioned along the sidewall and configured to receive a rotational input; and
the graphical output is further responsive to the rotational input.

11. The electronic watch of claim 10, wherein:
the sidewall further defines:
    a first passage extending from the recess into an interior volume of the housing; and
    a second passage extending from an exterior surface of the sidewall into the interior volume of the housing;
the modular sensing assembly further comprises:
    a retention bracket positioned along an interior surface of the sidewall; and
    a button member positioned between the cover and the translation sensor and extending at least partially through the first passage; and
the crown includes a shaft extending through the second passage.

12. The electronic watch of claim 11, wherein:
the translation sensor is coupled to the retention bracket and aligned with the first passage; and
the button member is configured to translate in response to the cover translating, thereby actuating the translation sensor.

13. The electronic watch of claim 11, wherein the modular sensing assembly further comprises a sealing member positioned along an inside surface of the recess and configured to deform in response to the cover translating.

14. The electronic watch of claim 13, wherein:
the sidewall further defines a third passage extending from the recess into the interior volume of the housing;
the modular sensing assembly further comprises a button retainer extending around the button member and coupled to the retention bracket via a fastener extending through the third passage; and
the sealing member extends around the button retainer and forms a seal between the button retainer and the housing.

15. The electronic watch of claim 13, wherein:
the sidewall further defines a third passage extending from the recess into the interior volume of the housing;
the modular sensing assembly further comprises a connector that operably couples the capacitive sensor to the processing unit and extends through the third passage and into the interior volume; and
the sealing member extends around the first passage and the third passage and is configured to prevent contaminants from entering the interior volume via the first passage or the third passage.

16. An electronic device comprising:
a housing defining a recess; and
a modular sensing assembly disposed in the recess, and comprising:
    an assembly enclosure comprising:
        a cover defining an input surface and configured to translate in response to a translational input; and
        a trim member extending around a perimeter of the cover;
    a touch sensor positioned at least partially within the assembly enclosure and configured to:
        detect a touch input on the input surface; and
        detect a fingerprint input on the input surface;
    an audio sensor positioned at least partially within the assembly enclosure and configured to detect an audio input through an opening in the cover;
    an electrocardiograph electrode disposed on an exterior surface of the cover and configured to detect an electrocardiograph signal;
    a dome switch positioned beneath the cover and configured to detect the translational input by actuating in response to the cover translating; and
    a sealing member positioned between the trim member and an inside surface of the recess, the sealing member configured to deform in response to the translational input.

17. The electronic device of claim 16, wherein the electrocardiograph electrode is positioned along a portion of the perimeter of the cover.

18. The electronic device of claim 17, wherein:
the portion of the perimeter of the cover is curved;
the electrocardiograph electrode conforms to a curvature of the portion of the perimeter of the cover; and
the electrocardiograph electrode at least partially surrounds a region of the cover that does not include the electrocardiograph electrode.

19. The electronic device of claim 18, wherein the portion of the perimeter of the cover defines a 180-degree curve.

20. The electronic device of claim 16, wherein the electrocardiograph electrode extends from the exterior surface of the cover and around an edge of the cover to a connector coupled to an interior surface of the cover.

* * * * *